United States Patent
Dyckman et al.

(10) Patent No.: US 11,046,646 B2
(45) Date of Patent: Jun. 29, 2021

(54) ALKYLPHENYL COMPOUNDS

(71) Applicant: BRISTOL-MYERS SQUIBB COMPANY, Princeton, NJ (US)

(72) Inventors: Alaric J. Dyckman, Lawrenceville, NJ (US); Ling Li, Pennington, NJ (US); John L. Gilmore, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/636,670

(22) PCT Filed: Aug. 8, 2018

(86) PCT No.: PCT/US2018/045691
§ 371 (c)(1),
(2) Date: Feb. 5, 2020

(87) PCT Pub. No.: WO2019/032632
PCT Pub. Date: Feb. 14, 2019

(65) Prior Publication Data
US 2021/0147357 A1 May 20, 2021

Related U.S. Application Data

(60) Provisional application No. 62/542,968, filed on Aug. 9, 2017.

(51) Int. Cl.
C07D 207/04 (2006.01)
A61K 31/40 (2006.01)
A61P 1/00 (2006.01)
C07D 207/16 (2006.01)

(52) U.S. Cl.
CPC .................. C07D 207/16 (2013.01)

(58) Field of Classification Search
CPC .......... C07D 207/16; A61P 1/00; A61K 31/40
See application file for complete search history.

(56) References Cited

U.S. PATENT DOCUMENTS

| | | | |
|---|---|---|---|
| 3,843,666 A | 10/1974 | Coombs et al. | |
| 5,670,522 A | 9/1997 | Lesson et al. | |
| 6,251,922 B1 | 6/2001 | Jahne et al. | |
| 7,115,545 B1 | 10/2006 | Witschel et al. | |
| 8,217,027 B2 * | 7/2012 | Wallace | A61P 25/00 514/210.17 |
| 8,492,441 B2 | 7/2013 | Legangneux | |
| 2004/0259904 A1 | 12/2004 | Tong et al. | |
| 2005/0027125 A1 | 2/2005 | Linden et al. | |
| 2007/0281963 A1 | 12/2007 | Fukumoto et al. | |
| 2009/0029947 A1 | 1/2009 | Wallace et al. | |
| 2010/0216762 A1 | 8/2010 | Harris et al. | |
| 2016/0052888 A1 | 2/2016 | Dyckman et al. | |

FOREIGN PATENT DOCUMENTS

| | | |
|---|---|---|
| EP | 223914 A1 | 9/2010 |
| EP | 2592071 A1 | 5/2013 |
| GB | 1354097 | 5/1974 |
| GB | 1354098 | 5/1974 |
| JP | 47016454 | 9/1972 |
| JP | 47022226 | 10/1972 |
| JP | 4899161 | 12/1973 |
| JP | 2004-18489 | 1/2004 |
| WO | WO9605828 A1 | 2/1996 |
| WO | WO199725317 A1 | 7/1997 |
| WO | WO199813356 A1 | 4/1998 |
| WO | WO199917769 A1 | 4/1999 |
| WO | WO200027822 A2 | 5/2000 |

(Continued)

OTHER PUBLICATIONS

Dinges, et al., "1,4-Dihydroindeno[1,2-c]pyrazoles with Acetylenic Side Chains as Novel and Potent Multitargeted Receptor Tyrosine Kinase Inhibitors with Low Affinity for the hERG Ion Channel", J. Med. Chem., 2007, vol. 50, pp. 2011-2029.

Ho, et al. "(6,7-Dimethoxy-2,4-dihydroindeno[1,2-c]pyrazol-3-yl)phenylamines: Platelet-Derived Growth Factor Receptor Tyrosine Kinase Inhibitors with Broad Antiproliferative Activity against Tumor Cells", J. Med. Chem., 2005, vol. 48, pp. 8163-8173.

International Preliminary Report on Patentability PCT/US2018/045691, dated Feb. 11, 2020.

Kumar, et al., "Efficient Routes to Pyrazolo[3,4-b]indoles and Pyrazolo[1,5-a]benzimidazoles via Palladium- and Copper-Catalyzed Intramolecular C_C and C—N Bond Formation", J. Org. Chem., 2009, vol. 74, pp. 7046-7051.

(Continued)

Primary Examiner — Kamal A Saeed
(74) Attorney, Agent, or Firm — Gary Greenblatt

(57) ABSTRACT

Disclosed are compounds of Formula (I): (I) or a salt thereof, wherein: X is —$CH_2$— or —C(O)—; $R_1$ is —OH or —OP(O)(OH)$_2$; L is a bond, —$CH_2$—, or —C(O)—; $R_2$ is n-$C_{6-8}$ alkyl; each $R_3$ is independently selected from Cl and —$CH_3$; and n is zero, 1, or 2; provided that if X is —$CH_2$—, then L is —$CH_2$— or —C(O)—. Also disclosed are methods of using such compounds as selective agonists for G protein coupled receptor $S1P_1$, and pharmaceutical compositions comprising such compounds. These compounds are useful in treating, preventing, or slowing the progression of diseases or disorders in a variety of therapeutic areas, such as autoimmune diseases and vascular disease.

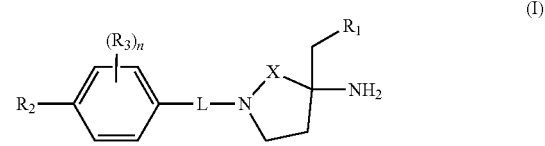

14 Claims, No Drawings

(56) References Cited

FOREIGN PATENT DOCUMENTS

| WO | WO200187846 A2 | 11/2001 |
| WO | WO2003061655 A1 | 7/2003 |
| WO | WO2003097609 A1 | 11/2003 |
| WO | WO2003105840 A2 | 12/2003 |
| WO | WO2005095387 A1 | 10/2005 |
| WO | WO2006052555 A2 | 5/2006 |
| WO | WO2008028168 A2 | 3/2008 |
| WO | WO2008039520 A1 | 4/2008 |
| WO | WO2008053300 A1 | 5/2008 |
| WO | WO2008094896 A1 | 8/2008 |
| WO | WO2008118790 A1 | 10/2008 |
| WO | WO2009078983 A1 | 6/2009 |
| WO | WO2009089305 A1 | 7/2009 |
| WO | WO2009123971 A1 | 10/2009 |
| WO | WO2010011316 A1 | 1/2010 |

OTHER PUBLICATIONS

Marcoux, et al., "Identification of potent tricyclic prodrug S1P1 receptor modulators", MedChemComm, 2017, vol. 8, pp. 725.

Ponomarev, et al., "Nature of the excited states of dialkylamino derivatives of aromatic and heteroaromatic compounds with annelated oxazole rings", Teoreticheskaya i Eksperimental'naya Khimiya, 1990, 26 (6), pp. 644-650.

Ponomarev, et al., "Spin-orbit interaction of their $\pi\pi^*$-states in molecules with annelated oxazole rings", Teoreticheskaya i Eksperimental'naya Khimiya, 1990, vol. 26 (4), pp. 403-406.

Rosen, et al., "Discovery of the first known small-molecule inhibitors of heme-regulated eukaryotic initiation factor $2\alpha$ (HRI) kinase", Bioorganic & Medicinal Chemistry Letters, 2009, vol. 19, pp. 6548-6551.

Shen, et al. "Discovery of Novel Tricyclic Full Agonists for the G-Protein-Coupled Niacin Receptor 109A with Minimized Flushing in Rats", J. Med. Chem, 2009, vol. 52, pp. 2567-2602.

Tao, et al.; "Discovery of 4'-(1,4-dihydro-indeno[1,2-c]pyrazol-3-yl)-benzonitriles and 4'-(1,4-dihydro-indenol[1,2-c] pyrazol-3-yl)-pryridine-2'-carbonitriles as potent checkpoint kinase 1 (Chk1) inhibitors", Bioorganic & Medicinal Chemistry Letters, 2007, vol. 17, pp. 5944-5951.

* cited by examiner

ALKYLPHENYL COMPOUNDS

CROSS REFERENCE TO RELATED APPLICATIONS

This application is a national phase application under 35 U.S.C. § 371 of International Patent Application No. PCT/US2018/045691, filed Aug. 8, 2018, which claims priority to U.S. Provisional Application No. 62/542,968, filed Aug. 9, 2017, which are expressly incorporated fully herein by reference.

The present invention generally relates to alkylphenyl compounds useful as $S1P_1$ agonists. Provided herein are alkylphenyl compounds, compositions comprising such compounds, and methods of their use. The invention further pertains to pharmaceutical compositions comprising at least one compound according to the invention that are useful for the treatment of conditions related to $S1P_1$ agonism, such as autoimmune diseases and vascular disease.

BACKGROUND OF THE INVENTION

Sphingosine-1-phosphate (S1P) has been demonstrated to induce many cellular effects, including those that result in platelet aggregation, cell proliferation, cell morphology, tumor cell invasion, endothelial cell and leukocyte chemotaxis, endothelial cell in vitro angiogenesis, and lymphocyte trafficking. S1P receptors are therefore good targets for a wide variety of therapeutic applications such as tumor growth inhibition, vascular disease, and autoimmune diseases. S1P signals cells in part via a set of G protein-coupled receptors named $S1P_1$ or S1P1, $S1P_2$ or S1P2, $S1P_3$ or S1P3, $S1P_4$ or S1P4, and $S1P_5$ or S1P5 (formerly called EDG-1, EDG-5, EDG-3, EDG-6, and EDG-8, respectively).

S1P is important in the entire human body as it is also a major regulator of the vascular and immune systems. In the vascular system, S1P regulates angiogenesis, vascular stability, and permeability. In the immune system, S1P is recognized as a major regulator of trafficking of T- and B-cells. S1P interaction with its receptor $S1P_1$ is needed for the egress of immune cells from the lymphoid organs (such as thymus and lymph nodes) into the lymphatic vessels. Therefore, modulation of S1P receptors was shown to be critical for immunomodulation, and S1P receptor modulators are novel immunosuppressive agents.

The $S1P_1$ receptor is expressed in a number of tissues. It is the predominant family member expressed on lymphocytes and plays an important role in lymphocyte trafficking. Downregulation of the $S1P_1$ receptor disrupts lymphocyte migration and homing to various tissues. This results in sequestration of the lymphocytes in lymph organs thereby decreasing the number of circulating lymphocytes that are capable of migration to the affected tissues. Thus, development of an $S1P_1$ receptor agent that suppresses lymphocyte migration to the target sites associated with autoimmune and aberrant inflammatory processes could be efficacious in a number of autoimmune and inflammatory disease states.

Among the five S1P receptors, $S1P_1$ has a widespread distribution and is highly abundant on endothelial cells where it works in concert with $S1P_3$ to regulate cell migration, differentiation, and barrier function. Inhibition of lymphocyte recirculation by non-selective S1P receptor modulation produces clinical immunosuppression preventing transplant rejection, but such modulation also results in transient bradycardia. Studies have shown that $S1P_1$ activity is significantly correlated with depletion of circulating lymphocytes. In contrast, $S1P_3$ receptor agonism is not required for efficacy. Instead, $S1P_3$ activity plays a significant role in the observed acute toxicity of nonselective S1P receptor agonists, resulting in the undesirable cardiovascular effects, such as bradycardia and hypertension. (See, e.g., Hale et al., *Bioorg. Med. Chem. Lett.*, 14:3501 (2004); Sanna et al., *J. Biol. Chem.*, 279:13839 (2004); Anliker et al., *J. Biol. Chem.*, 279:20555 (2004); Mandala et al., *J. Pharmacol. Exp. Ther.*, 309:758 (2004).)

An example of an $S1P_1$ agonist is FTY720. This immunosuppressive compound FTY720 (JPI 1080026-A) has been shown to reduce circulating lymphocytes in animals and humans, and to have disease modulating activity in animal models of organ rejection and immune disorders. The use of FTY720 in humans has been effective in reducing the rate of organ rejection in human renal transplantation and increasing the remission rates in relapsing remitting multiple sclerosis (see Brinkman et al., *J. Biol. Chem.*, 277:21453 (2002); Mandala et al., *Science*, 296:346 (2002); Fujino et al., *J. Pharmacol. Exp. Ther.*, 305:45658 (2003); Brinkman et al., *Am. J. Transplant*, 4:1019 (2004); Webb et al., *J. Neuroimmunol*, 153:108 (2004); Morris et al., *Eur. J. Immunol.*, 35:3570 (2005); Chiba, *Pharmacology & Therapeutics*, 108:308 (2005); Kahan et al., *Transplantation*, 76:1079 (2003); and Kappos et al., *N Engl. J. Med.*, 335:1124 (2006)). Subsequent to its discovery, it has been established that FTY720 is a prodrug, which is phosphorylated in vivo by sphingosine kinases to a more biologically active agent that has agonist activity at the $S1P_1$, $S1P_3$, $S1P_4$, and $S1P_5$ receptors. It is this activity on the S1P family of receptors that is largely responsible for the pharmacological effects of FTY720 in animals and humans.

Clinical studies have demonstrated that treatment with FTY720 results in bradycardia in the first 24 hours of treatment (Kappos et al., *N Engl. J. Med.*, 335:1124 (2006)). The observed bradycardia is commonly thought to be due to agonism at the S1P3 receptor. This conclusion is based on a number of cell based and animal experiments. These include the use of S1P3 knockout animals which, unlike wild type mice, do not demonstrate bradycardia following FTY720 administration and the use of $S1P_1$ selective compounds. (Hale et al., *Bioorg. Med. Chem. Lett.*, 14:3501 (2004); Sanna et al., *J. Biol. Chem.*, 279:13839 (2004); and Koyrakh et al., *Am. J. Transplant.*, 5:529 (2005)). The following applications have described compounds as $S1P_1$ agonists: WO 03/061567 (U.S. Publication No. 2005/0070506), WO 03/062248 (U.S. Pat. No. 7,351,725), WO 03/062252 (U.S. Pat. No. 7,479,504), WO 03/073986 (U.S. Pat. No. 7,309,721), WO 03/105771, WO 05/058848, WO 05/000833, WO 05/082089 (U.S. Publication No. 2007/0203100), WO 06/047195, WO 06/100633, WO 06/115188, WO 06/131336, WO 2007/024922, WO 07/109330, WO 07/116866, WO 08/023783 (U.S. Publication No. 2008/0200535), WO 08/029370, WO 08/114157, WO 08/074820, WO 09/043889, WO 09/057079, WO 2014/130752, WO 2016/028959, and U.S. Pat. No. 6,069,143. Also see Hale et al., *J. Med. Chem.*, 47:6662 (2004).

There still remains a need for compounds useful as $S1P_1$ agonists and yet having selectivity over S1P3.

Applicants have found potent compounds that have activity as $S1P_1$ agonists. Further, applicants have found compounds that have activity as $S1P_1$ agonists and are selective over S1P3. These compounds are provided to be useful as pharmaceuticals with desirable stability, bioavailability, therapeutic index, and toxicity values that are important to their drugability.

SUMMARY OF THE INVENTION

The present invention provides substituted oxime ether compounds of Formula (I), which are useful as modulators of S1P$_1$ activity, including salts thereof.

The present invention also provides pharmaceutical compositions comprising a compound of Formula (I) and/or a pharmaceutically acceptable salt thereof; and a pharmaceutically acceptable carrier.

The present invention also provides a method of treating a disease or disorder associated with the activity of G protein-coupled receptor S1P$_1$, the method comprising administering to a mammalian patient a compound of Formula (I) and/or a pharmaceutically acceptable salt thereof.

The present invention also provides processes and intermediates for making the compounds of Formula (I) and/or salts thereof.

The present invention also provides a compound of Formula (I) and/or a pharmaceutically acceptable salt thereof, for use in therapy.

The present invention also provides the use of the compounds of Formula (I) and/or pharmaceutically acceptable salts thereof, for the manufacture of a medicament for the treatment or prophylaxis of S1P$_1$ receptor-related conditions, such as autoimmune and vascular diseases.

The compounds of Formula (I) and compositions comprising the compounds of Formula (I) may be used in treating, preventing, or curing various S1P$_1$ related conditions. Pharmaceutical compositions comprising these compounds are useful in treating, preventing, or slowing the progression of diseases or disorders in a variety of therapeutic areas, such as autoimmune and vascular diseases.

These and other features of the invention will be set forth in expanded form as the disclosure continues.

DETAILED DESCRIPTION

The first aspect of the present invention provides at least one compound of Formula (I):

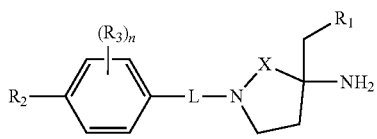
(I)

or a salt thereof, wherein:

X is —CH$_2$— or —C(O)—;

L is a bond, —CH$_2$—, or —C(O)—;

R$_1$ is —OH or —OP(O)(OH)$_2$;

R$_2$ is n-C$_{6-8}$ alkyl;

each R$_3$ is independently selected from Cl and —CH$_3$; and n is zero, 1, or 2; provided that if X is —CH$_2$—, then L is —CH$_2$— or —C(O)—.

One embodiment provides a compound of Formula (I) or a salt thereof, wherein X is —CH$_2$—; L is —CH$_2$— or —C(O)—; R$_1$, R$_2$, R$_3$, and n are defined in the first aspect. Compounds of this embodiment have the structure of Formula (II):

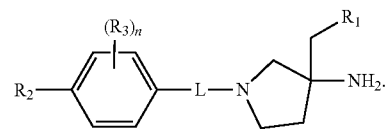
(II)

One embodiment provides a compound of Formula (I) or a salt thereof, wherein X is —CH$_2$—; L is —CH$_2$—; and R$_1$, R$_2$, R$_3$, and n are defined in the first aspect. Compounds of this embodiment have the structure of Formula (IIa):

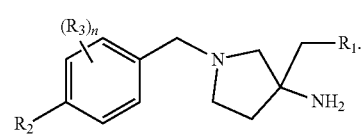
(IIa)

One embodiment provides a compound of Formula (I) or a salt thereof, wherein X is —CH$_2$—; L is —C(O)—; and R$_1$, R$_2$, R$_3$, and n are defined in the first aspect. Compounds of this embodiment have the structure of Formula (IIb):

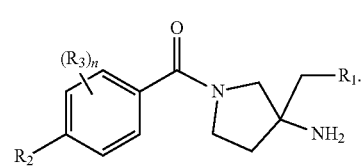
(IIb)

One embodiment provides a compound of Formula (I) or a salt thereof, wherein X is —C(O)—; and L, R$_1$, R$_2$, R$_3$, and n are defined in the first aspect. Compounds of this embodiment have the structure of Formula

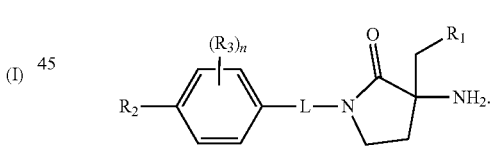
(III)

One embodiment provides a compound of Formula (I) or a salt thereof, wherein X is —C(O)—; L is a bond; and R$_1$, R$_2$, R$_3$, and n are defined in the first aspect. Compounds of this embodiment have the structure of Formula (Ma):

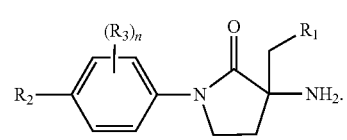
(IIIa)

One embodiment provides a compound of Formula (I) or a salt thereof, wherein X is —C(O)—; L is —CH$_2$—; and R$_1$, R$_2$, R$_3$, and n are defined in the first aspect. Compounds of this embodiment have the structure of Formula (IIIb):

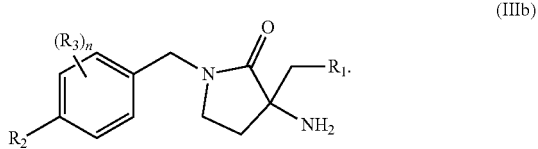

(IIIb)

One embodiment provides a compound of Formula (I) or a salt thereof, wherein X is —C(O)—; L is —C(O)—; and $R_1$, $R_2$, $R_3$, and n are defined in the first aspect. Compounds of this embodiment have the structure of Formula (IIIc):

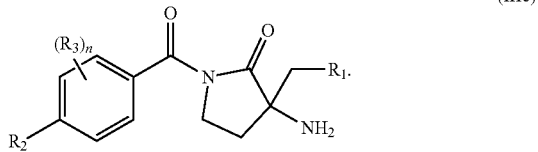

(IIIc)

One embodiment provides a compound of Formula (I) or a salt thereof, wherein X is —C(O)—; L is —CH$_2$— or —C(O)—; $R_1$ is —OH or —OP(O)(OH)$_2$; $R_2$ is n-C$_{6-8}$ alkyl; each $R_3$ is independently selected from Cl and —CH$_3$; and n is zero, 1, or 2. Included in this embodiment are compounds in which $R_2$ is n-octyl.

One embodiment provides a compound of Formula (I) or a salt thereof, wherein X is —C(O)—; L is a bond or —CH$_2$—; $R_1$ is —OH or —OP(O)(OH)$_2$; $R_2$ is n-C$_{6-8}$ alkyl; each $R_3$ is independently selected from Cl and —CH$_3$; and n is zero, 1, or 2. Included in this embodiment are compounds in which $R_2$ is n-octyl.

One embodiment provides a compound of Formula (I) or a salt thereof, wherein X is —C(O)—; L is a bond or —C(O)—; $R_1$ is —OH or —OP(O)(OH)$_2$; $R_2$ is n-C$_{6-8}$ alkyl; each $R_3$ is independently selected from Cl and —CH$_3$; and n is zero, 1, or 2. Included in this embodiment are compounds in which $R_2$ is n-octyl.

One embodiment provides a compound of Formula (I) or a salt thereof, wherein X is —CH$_2$— or —C(O)—; L is —CH$_2$—; $R_1$ is —OH or —OP(O)(OH)$_2$; $R_2$ is n-C$_{7-8}$ alkyl; each $R_3$ is independently selected from Cl and —CH$_3$; and n is zero, 1, or 2. Included in this embodiment are compounds in which $R_2$ is n-octyl.

One embodiment provides a compound of Formula (I) or a salt thereof, wherein X is —CH$_2$— or —C(O)—; L is —C(O)—; $R_1$ is —OH or —OP(O)(OH)$_2$; $R_2$ is n-C$_{7-8}$ alkyl; each $R_3$ is independently selected from Cl and —CH$_3$; and n is zero, 1, or 2. Included in this embodiment are compounds in which $R_2$ is n-octyl.

One embodiment provides a compound of Formula (I) or a salt thereof, wherein X is —CH$_2$— or —C(O)—; L is a bond, —CH$_2$—, or —C(O)—; $R_1$ is —OH; $R_2$ is n-C$_{6-8}$ alkyl; each $R_3$ is independently selected from Cl and —CH$_3$; and n is zero, 1, or 2; provided that if X is —CH$_2$—, then L is —CH$_2$— or —C(O)—. Included in this embodiment are compounds in which $R_2$ is n-octyl.

One embodiment provides a compound of Formula (I) or a salt thereof, wherein X is —CH$_2$— or —C(O)—; L is a bond, —CH$_2$—, or —C(O)—; $R_1$ is —OP(O)(OH)$_2$; $R_2$ is n-C$_{6-8}$ alkyl; each $R_3$ is independently selected from Cl and —CH$_3$; and n is zero, 1, or 2; provided that if X is —CH$_2$—, then L is —CH$_2$— or —C(O)—. Included in this embodiment are compounds in which $R_2$ is n-octyl.

One embodiment provides a compound of Formula (I) or a salt thereof, wherein X is X is —CH$_2$— or —C(O)—; L is a bond, —CH$_2$—, or —C(O)—; $R_1$ is —OH or —OP(O)(OH)$_2$; $R_2$ is n-C$_{7-8}$ alkyl; each $R_3$ is independently selected from Cl and —CH$_3$; and n is zero, 1, or 2; provided that if X is —CH$_2$—, then L is —CH$_2$— or —C(O)—. Included in this embodiment are compounds in which $R_2$ is n-octyl.

One embodiment provides a compound of Formula (I) or a salt thereof, wherein X is X is —CH$_2$— or —C(O)—; L is a bond, —CH$_2$—, or —C(O)—; $R_1$ is —OH or —OP(O)(OH)$_2$; $R_2$ is n-C$_{6-8}$ alkyl; each $R_3$ is independently selected from Cl and —CH$_3$; and n is 1 or 2; provided that if X is —CH$_2$—, then L is —CH$_2$— or —C(O)—. Included in this embodiment are compounds having the structures:

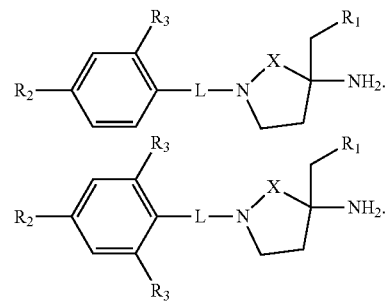

One embodiment provides a compound of Formula (I) or a salt thereof, wherein X is —CH$_2$— or —C(O)—; L is a bond, —CH$_2$—, or —C(O)—; $R_1$ is —OH or —OP(O)(OH)$_2$; $R_2$ is n-C$_{6-8}$ alkyl; each $R_3$ is —CH$_3$; and n is 1 or 2; provided that if X is —CH$_2$—, then L is —CH$_2$— or —C(O)—.

One embodiment provides a compound of Formula (I) or a salt thereof, wherein X is —CH$_2$— or —C(O)—; L is a bond, —CH$_2$—, or —C(O)—; $R_1$ is —OH or —OP(O)(OH)$_2$; $R_2$ is n-C$_{6-8}$ alkyl; each $R_3$ is —Cl; and n is 1 or 2; provided that if X is —CH$_2$—, then L is —CH$_2$— or —C(O)—.

One embodiment provides a compound of Formula (I) or a salt thereof, wherein said compound is: (3-amino-3-(hydroxymethyl)pyrrolidin-1-yl)(4-octylphenyl) methanone (1); (3-amino-1-(4-octylbenzyl)pyrrolidin-3-yl)methanol (2); 3-amino-3-(hydroxymethyl)-1-(4-octylbenzyl)pyrrolidin-2-one, TFA (3-5); 3-amino-3-(hydroxymethyl)-1-(4-octylphenyl)pyrrolidin-2-one (6-8); 3-amino-3-(hydroxymethyl)-1-(2-methyl-4-octylphenyl)pyrrolidin-2-one (9); 3-amino-3-(hydroxymethyl)-1-(2-methyl-4-octylphenyl) pyrrolidin-2-one (10); 3-amino-3-(hydroxymethyl)-1-(2-methyl-4-octylphenyl)pyrrolidin-2-one (11); 3-amino-1-(2, 6-dichloro-4-octylphenyl)-3-(hydroxymethyl)pyrrolidin-2-one (12); or 3-amino-1-(2,6-dimethyl-4-octylphenyl)-3-(hydroxymethyl)pyrrolidin-2-one (13).

One embodiment provides a compound of Formula (I) or a salt thereof, wherein said compound is: (3-amino-1-(4-octylbenzyl)-2-oxopyrrolidin-3-yl)methyl dihydrogen phosphate (14); (3-amino-1-(2,6-dimethyl-4-octylphenyl)-2-oxopyrrolidin-3-yl)methyl dihydrogen phosphate (15); (3-amino-1-(2,6-dichloro-4-octylphenyl)-2-oxopyrrolidin-3-yl)methyl dihydrogen phosphate (16); (3-amino-1-(2-methyl-4-octylphenyl)-2-oxopyrrolidin-3-yl)methyl dihydrogen phosphate (17); or (3-amino-1-(4-octylphenyl)-2-oxopyrrolidin-3-yl)methyl dihydrogen phosphate (18).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "n-$C_{6-8}$ alkyl" as used herein, refers to straight-chain saturated aliphatic hydrocarbon groups containing from 6 to 8 carbon atoms. Examples of n-$C_{6-8}$ alkyl groups include n-hexyl, n-heptyl, and n-octyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist to $S1P_1$, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) and/or pharmaceutically acceptable salts thereof can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof.

While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one pharmaceutically acceptable salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease. Thus it has been observed that therapeutic agents which act on the immune system or certain cell types of the immune system (such as B-lymphocytes, and T lymphocytes, T cells) may have utility in more than one autoimmune disease.

It is well recognized in the art, including the literature references cited herein, that S1P receptors are good targets for a wide variety of therapeutic applications, including autoimmune diseases. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other processes. Therefore, compounds that act on some S1P receptor family members while having diminished or no activity at other family members are desirable and are expected to provide a therapeutic effect with an improved side effect profile (i.e., reduction or elimination of unwanted side effects).

As used herein, the term "agonist" in reference to $S1P_1$ refers to an agent which exerts pharmacological effects such as decreased motility of T cells, decreased trafficking of T cells, or decreased egress of T cells from lymphoid tissues. (Rosen et al., *Trends in Immunology*, 28:102 (2007)).

By virtue of their $S1P_1$ activity as agonists, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy, and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, juvenile idiopathic arthritis, systemic lupus erythematosus, cutaneous lupus erythematosus (discoid lupus erythematosus, subacute lupus erythematosus) and lupus nephritis, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, psoriatic arthritis, atopic dermatitis, contact dermatitis, eczematous dermatitis, seborrheic dermatitis, lichen planus, pemphigus, bullous pemphigoid, epidermolysis bullosa, urticaria, angioedemas, vasculitis including ANCA-associated vasculitis, giant cell arteritis, Takayasu's arteritis, microscopic poliangiitis, central nervous system vasculitis, Churg-Strauss Syndrome, and rheumatoid vasculitis, erythema, cutaneous eosinophilia, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis *nodosa*, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia *senilis* by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, neuropathic pain, chronic bacterial infection, thrombocytopenia, IgA nephropathy, mesangioproliferative glomerulonephritis, IgG4-related disease, ankylosing spondylitis, and relapsing polychondritis. Juvenile idiopathic arthritis includes oligoarthritis-onset juvenile idiopathic arthritis, polyarthritis-onset juvenile idiopathic arthritis, systemic-onset juvenile idiopathic arthritis, juvenile psoriatic arthritis, and enthesitis-related juvenile idiopathic arthritis.

One embodiment provides a method for treating autoimmune and/or inflammatory diseases, comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of autoimmune and/or inflammatory diseases. In another embodiment, provided is the use of the compounds of Formula (I) or pharmaceutically acceptable salts thereof, for the manufacture of a medicament for the treatment or prophylaxis of autoimmune and/or inflammatory disease. A therapeutically effective amount may be employed in these embodiments. Preferably, in these embodiments, the autoimmune and inflammatory diseases are selected from multiple sclerosis, rheumatoid arthritis, inflammatory bowel disease (including Crohn's disease and ulcerative colitis), psoriasis, and as an agent to prevent the rejection of transplanted organs. The method of the present embodiment includes administration of a therapeutically effect amount of a compound of Formula (I) or a pharmaceutically effective salt thereof.

In another embodiment, a method for treating vascular disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of vascular disease. In another embodiment, provided is the use of the compounds of Formula (I) or pharmaceutically acceptable salts thereof, for the manufacture of a medicament for treatment of vascular disease. A therapeutically effective amount may be employed in these embodiments. Preferably, in these embodiments, the vascular disease is selected from atherosclerosis and ischemia reperfusion injury.

In another embodiment, a method for treating inflammatory bowel disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of inflammatory bowel disease. In another embodiment, provided is the use of the compounds of Formula (I) or pharmaceutically acceptable salts thereof, for the manufacture of a medicament for treatment of inflammatory bowel disease. A therapeutically effective amount may be employed in these embodiments. Preferably, in these embodiments, the inflammatory bowel disease is selected from Crohn's disease, ulcerative colitis, collagenous colitis, lymphocytic colitis, ischaemic colitis, diversion colitis, Behçet's disease, and indeterminate colitis.

In another embodiment, a method for treating lupus is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of lupus. In another embodiment, provided is the use of the compounds of Formula (I) or pharmaceutically acceptable salts thereof, for the manufacture of a medicament for treatment of lupus. A therapeutically effective amount may be employed in these embodiments. Lupus includes systemic lupus erythematosus, cutaneous lupus erythematosus, discoid lupus erythematosus, subacute lupus erythematosus and lupus nephritis.

In another embodiment, a method for treating multiple sclerosis is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of multiple sclerosis. In another embodiment, provided is the use of the compounds of Formula (I) or pharmaceutically acceptable salts thereof, for the manufacture of a medicament for treatment of multiple sclerosis. A therapeutically effective amount may be employed in these embodiments. Preferably, in these embodiments, multiple sclerosis includes relapsing remitting multiple sclerosis, primary progressive multiple sclerosis, secondary progressive multiple sclerosis, and progressive relapsing multiple sclerosis.

The methods of treating S1P1-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to act as an agonist at the S1P1 receptor. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased efficacy, or some other beneficial effect of the combination compared with the individual components.

Exemplary of such other therapeutic agents include corticosteroids or glucocorticoids such as dexamethasone, methylprednisolone, prednisolone, and prednisone; PDE4 inhibitors such as rolipram, cilomilast, roflumilast, and oglemilast; cytokine-suppressive anti-inflammatory drugs (CSAIDs) and inhibitors of p38 kinase, 4-substituted imidazo [1,2-A]quinoxalines as disclosed in U.S. Pat. No. 4,200,750; antibodies or fusion proteins directed to cell surface molecules such as CD2, CD3, CD4, CD8, CD20 such as RITUXAN®, CD25, CD30, CD40, CD69, CD80 (B7.1), CD86 (B7.2), CD90, CTLA, for example abatacept (ORENCIA®), belatacept, or their ligands including CD154 (GP39, or CD40L); antibodies to, fusion proteins, or soluble receptors of human cytokines or growth factors, for example, TNF such as, infliximab (REMICADE®), etanercept (Embrel), adalimumab (HUMIRA®), LT, Il-1 such as anakinra (KINERET®) (an IL-1 receptor antagonist), IL-2, IL-4, IL-5, 11-6, such as CNTO 328 (a chimeric anti-IL-6 antibody), 11-7, 11-8, 11-12, Il-15, 11-16, 11-17, 11-21, 11-23 such as Ustekinumab (a human anti-IL-12/23 monoclonal antibody), and interferons such as interferon beta 1a (AVONEX®, REBIF®), interferon beta 1b (BETASERON®); integrin receptor antagonists such as TYSABRI®; polymeric agents such as glatiramer acetate (COPAXONE®); sulfasalazine, mesalamine, hydroxychloroquine, non-steroidal antiinflammatory drugs (NSAIDs) such as salicylates including aspirin, salsalate, and magnesium salicylate, and non-salicylates such as, ibuprofen, naproxen, meloxicam, celecoxib and rofecoxib; antiviral agents such as abacavir; antiproliferative agents such as methotrexate, mercaptopurine, leflunomide, cyclosporine, mycophenolate, FK506 (tacrolimus, PROGRAF®); cytotoxic drugs such as azathioprine and cyclophosphamide; nuclear translocation inhibitors, such as deoxyspergualin (DSG); gold containing products such as auronofin; penicllamine, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a desired compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1 or I1, Int. 2 or I2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

ABBREVIATIONS

Ac acetyl
AcOH acetic acid
anhyd. anhydrous
aq. aqueous
Bu butyl
Boc tert-butoxycarbonyl
CV Column Volumes
DCM dichloromethane
DEA diethylamine
DME dimethyl ether
DMF dimethylformamide
DMSO dimethylsulfoxide
EtOAc ethyl acetate
Et ethyl
EtOH ethanol
$H_2$ hydrogen
h, hr or hrs hour(s)
hex hexane
i iso
HCl hydrochloric acid
HPLC high pressure liquid chromatography
LC liquid chromatography
M molar
mM millimolar
Me methyl
MeCN acetonitrile
MeOH methanol
MHz megahertz
min. minute(s)
mins minute(s)
$M^{+1}$ $(M+H)^+$
MS mass spectrometry
n or N normal
NBS n-bromosuccinimide
nm nanometer
nM nanomolar
Pd/C palladium on carbon Ph phenyl
Pr propyl
PSI pounds per square inch
ret. time retention time
sat. saturated
SFC supercritical fluid chromatography
TEA triethylamine
TFA trifluoroacetic acid
THF tetrahydrofuran HPLC Conditions Condition G: Column: Waters Acquity BEH C18 2.1×50 mm 1.7 um; Linear gradient of 0-100% solvent B over 3 min, then 0.75 min hold at 100% B; Flow rate: 1.11 mL/min; Solvent A: 5:95 acetonitrile:water with 10 mM ammonium acetate; Solvent B: 95:5 acetonitrile:water with 10 mM ammonium acetate; Products detected at 220 wavelength.

Condition JG-G: Column: Waters Acquity BEH C18 2.1×50 mm 1.7 um; Linear gradient of 0-100% solvent B over 3 min, then 0.75 min hold at 100% B; Flow rate: 1.11 mL/min; Solvent A: 5:95 acetonitrile:water with 10 mM ammonium acetate; Solvent B: 95:5 acetonitrile:water with 10 mM ammonium acetate; Products detected at 220 nm wavelength.

Condition JG-H: Column: Sunfire C18, (150×3.0 mm), 3.5 μm; Linear gradient of 10 to 100% solvent B over 25 min, then 5 min hold at 100% B; Flow rate: 1 mL/min; Buffer: 0.5% TFA, in water with pH adjusted to 2.5 using dilute ammonia; Solvent A: Buffer: acetonitrile (95:5); Solvent B: Buffer: acetonitrile (5:95); Products detected at 220/254 nm.

Condition JG-I: Column: Xbridge Phenyl, (150×3.0 mm), 3.5 μm; Linear gradient of 10 to 100% solvent B over 25 min, then 5 min hold at 100% B; Flow rate: 1 mL/min; Buffer: 0.5% TFA, in water with pH adjusted to 2.5 using dilute ammonia; Solvent A: Buffer: acetonitrile (95:5); Solvent B: Buffer: acetonitrile (5:95); Products detected at 220/254 nm.

Condition JG-CC: Column=Waters Sunfire C18 2.1×50 mm 5 u (4 min. grad) Start % B=0; Final % B=100; Gradient Time=4 min; Flow Rate=1 ml/min; Wavelength=220; Solvent Pair=MeOH—H$_2$O-TFA; Solvent A=10% MeOH-90% H$_2$O-0.1% TFA; Solvent B=90% MeOH-10% H$_2$O-0.1% TFA;

Example 1

(3-amino-3-(hydroxymethyl)pyrrolidin-1-yl)(4-octylphenyl)methanone

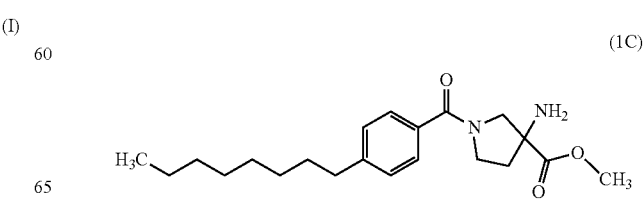

(I)

Preparation 1A: 3-((tert-butoxycarbonyl)amino)-1-(4-octylbenzoyl)pyrrolidine-3-carboxylic acid

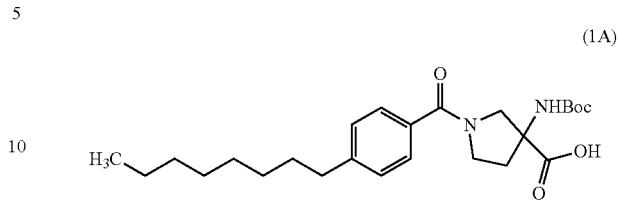

(1A)

A solution was prepared by dissolving 4-octylbenzoic acid (400 mg, 1.707 mmol) into DMF (6 mL) and CH$_2$Cl$_2$ (6 mL) cosolvent. To this solution was added N1-((ethylimino)methylene)-N3,N3-dimethylpropane-1,3-diamine hydrochloride (344 mg, 1.792 mmol) and HOBT (274 mg, 1.792 mmol). The mixture was allowed to stir at room temperature for 1 hour. Next, 3-(tert-butoxycarbonylamino) pyrrolidine-3-carboxylic acid (393 mg, 1.707 mmol) was added in one portion. The mixtures stirred at room temperature for 3 hours at which time LC-MS showed the reaction was completed. The crude material was purified via silica gel chromatography to afford the desired material (480 mg, 63% yield). HPLC Ret. Time=1.12 min (condition G), LC/MS M$^{+1}$=447.3.

Preparation 1B:
3-amino-1-(4-octylbenzoyl)pyrrolidine-3-carboxylic acid

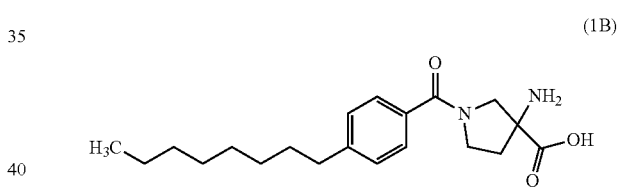

(1B)

A solution was prepared by dissolving 3-(tert-butoxycarbonylamino)-1-(4-octylbenzoyl)pyrrolidine-3-carboxylic acid (480 mg, 1.075 mmol) into CH$_2$Cl$_2$ (10 mL). TFA (5 mL, 64.9 mmol) was added and the mixture was stirred at room temperature for 2 hours at which time LC-MS analysis showed the reaction was completed. The crude material was concentrated and neutralized with saturated NaHCO$_3$, then extracted twice with ethyl acetate. The combined organic layers were dried over Na$_2$SO$_4$ and concentrated to afford 130 mg of Preparation 1B (yield 38%). HPLC Ret. Time=0.85 min (condition G), LC/MS M$^{+1}$=347.2.

Preparation 1C: Methyl 3-amino-1-(4-octylbenzoyl) pyrrolidine-3-carboxylate (1C)

3-(tert-butoxycarbonylamino)-1-(4-octylbenzoyl)pyrrolidine-3-carboxylic acid (39 mg, 0.11 mmol) was dissolved in CH$_2$Cl$_2$ (2 mL). The solution was cooled down to 0° C. with an ice water bath, then oxalyl dichloride (17.5 mg, 0.14 mmol) was added followed by 2 drops of DMF. The mixture stirred at 0° C. for 5 mins, before CH$_2$Cl$_2$ was evaporated by air flow and 2 ml of MeOH was added. The mixtures stirred overnight. The crude material was partitioned between EtOAc and saturated aqueous NaHCO$_3$. The organic layer was then dried over Na$_2$SO$_4$, concentrated and used directly in next step. HPLC Ret. Time=0.89 min (condition G), LC/MS M$^{+1}$=361.2.

Example 1

Methyl 3-amino-1-(4-octylbenzoyl)pyrrolidine-3-carboxylate (30 mg, 0.083 mmol) was dissolved into MeOH (2 mL). The solution was cooled down to 0° C. and then NaBH$_4$ (12.59 mg, 0.333 mmol) was added. The mixture was stirred at 0° C. for 1 hour at which time LC-MS analysis showed the reaction to be complete. The reaction was quenched with 1N HCl and the solution was concentrated. The crude material was purified on preparative HPLC (Column: YMC C18 Sum 30*75 mm; SolA: 10% MeOH-90% H$_2$O-0.1% TFA; SolB: 90% MeOH-10% H$_2$O-0.1% TFA) to afford Example 1 as a yellow oil (15 mg, 40% yield). HPLC Ret. Time=0.85 (condition G); LC/MS M$^{+1}$=333.2. $^1$H NMR (400 MHz, MeOD) δ ppm 7.47 (2H, br. s.), 7.30 (2H, d, J=8.14 Hz), 3.61-3.90 (6H, m), 2.66 (2H, t, J=7.70 Hz), 2.24 (2H, br. s.), 1.56-1.71 (2H, m), 1.20-1.42 (11H, m), 0.84-0.95 (3H, m).

Example 2

(3-amino-1-(4-octylbenzyl)pyrrolidin-3-yl)methanol

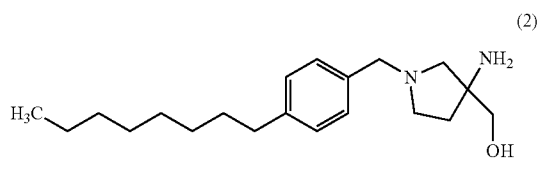 [SMILES: CCCCCCCCc1ccc(CN2CCC(N)(CO)C2)cc1]

(2)

Preparation 2A: 3-((tert-butoxycarbonyl)amino)-1-(4-octylbenzyl)pyrrolidine-3-carboxylic acid

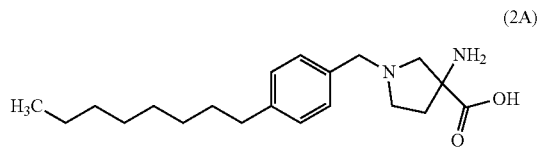 [SMILES: CCCCCCCCc1ccc(CN2CCC(N)(C(=O)O)C2)cc1]

(2A)

4-Octylbenzaldehyde (350 mg, 1.603 mmol) and 3-(tert-butoxycarbonylamino) pyrrolidine-3-carboxylic acid (554 mg, 2.405 mmol) were dissolved into MeOH (20 mL) in a 200 ml flask. A drop of AcOH was added and the mixture was stirred at room temperature for 20 min., before sodium triacetoxyborohydride (1359 mg, 6.41 mmol) was added in portions. The mixture was stirred at room temperature for 3 hours at which time LC-MS shows partial conversion of the starting material. Another 0.3 eq. of sodium triacetoxyborohydride was added and the reaction mixture was stirred at room temperature over night. The reaction was quenched with 1N HCl (5 mL). The reaction mixture was stirred at room temperature. The MeOH was evaporated and saturated aqueous NaHCO$_3$ (10 mL) was added to adjust pH to approximately 5. The mixture was extracted with ethyl acetate and the organic layer was concentrated to provide 490 mg (yield: 70%) of Preparation 2A. HPLC Ret. Time=0.97 min (condition G); LC/MS M$^{+1}$=[433.3].

Example 2

Into dry THF (2 ml) was dissolved 3-(tert-butoxycarbonylamino)-1-(4-octylbenzyl)pyrrolidine-3-carboxylic acid (30 mg, 0.069 mmol). The solution was cooled to 0° C. and BH$_3$.THF (0.208 mL, 0.208 mmol) was added slowly. The mixture was stirred at 0° C. for 2 hours at which time LC-MS showed partial conversion of starting material. Additional BH$_3$.THF (1.0 equivalent) was added and the reaction mixture was stirred for 2 hours, at which time HPLC analysis of the reaction indicated completion. The reaction was quenched by the addition of 4 N HCl in dioxane (1 ml). The reaction mixture was stirred at room temperature overnight. The crude material was purified with reverse phase HPLC to afford (3-amino-1-(4-octylbenzyl)pyrrolidin-3-yl) methanol as a white solid (2.4 mg, 10.4% yield). HPLC Ret. Time=0.84 min (condition G); LC/MS M$^{+1}$=319.2. $^1$H NMR (400 MHz, MeOD) δ ppm 7.25 (2H, s), 7.17 (2H, s), 2.73-2.84 (1H, m), 2.55-2.68 (4H, m), 2.39-2.45 (1H, m), 1.85-1.96 (1H, m), 1.57-1.70 (3H, m), 1.26-1.41 (12H, m), 0.93 (3H, s).

Example 3

3-amino-3-(hydroxymethyl)-1-(4-octylbenzyl)pyrrolidin-2-one, TFA

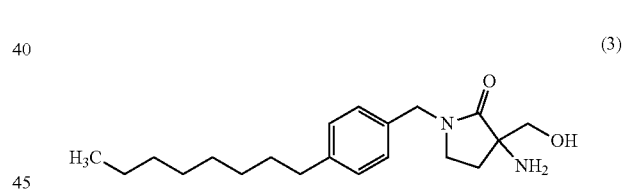

(3)

Preparation 3A: Ethyl 3-bromo-2-oxopyrrolidine-3-carboxylate

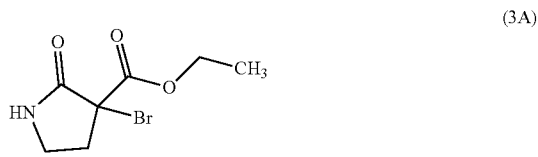

(3A)

To a mixture of ethyl 2-oxopyrrolidine-3-carboxylate (500 mg, 3.18 mmol) in THF (10 mL) was added sodium hydride (191 mg, 7.95 mmol). After 30 minutes, DMSO (10.00 mL) was added to help solubilize the material. Next, NBS (849 mg, 4.77 mmol) was added. The reaction mixture was stirred for 2 hours. The reaction mixture was diluted with ethyl acetate and washed with saturated aqueous NaCl. The organic layer was dried over MgSO$_4$, filtered and concentrated. The crude material was purified on a silica gel cartridge (40 g) using an EtOAc/Hexane gradient (0-100% EtOAc over 10CV). Isolated product fractions were concentrated and dried in vacuo to afford 330 mg of ethyl 3-bromo-2-oxopyrrolidine-3-carboxylate.

Preparation 3B: Ethyl 3-azido-2-oxopyrrolidine-3-carboxylate

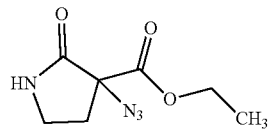

(3B)

To a mixture of ethyl 3-bromo-2-oxopyrrolidine-3-carboxylate (330 mg, 1.398 mmol) in DME (3 mL) was added sodium azide (136 mg, 2.097 mmol). The reaction mixture was heated to 90° C. overnight. The reaction mixture was diluted with ethyl acetate and washed with saturated aqueous NaCl. The organic layer was dried over MgSO₄, filtered and concentrated to afford 260 mg of ethyl 3-azido-2-oxopyrrolidine-3-carboxylate.

Preparation 3C: Ethyl 3-azido-1-(4-octylbenzyl)-2-oxopyrrolidine-3-carboxylate

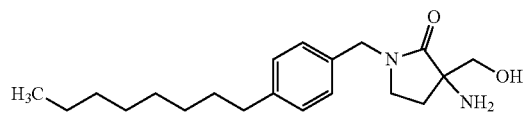

(3C)

To a mixture of ethyl 3-azido-2-oxopyrrolidine-3-carboxylate (90 mg, 0.454 mmol) in THF (5 mL) was added sodium hydride (23.61 mg, 0.590 mmol). After bubbling ceased, 1-(bromomethyl)-4-octylbenzene (232 mg, 0.817 mmol) was added. The mixture was stirred for 3 hours. The reaction was quenched with water. The reaction mixture was diluted with ethyl acetate and washed with saturated aqueous NaCl. The organic layer was dried over MgSO₄, filtered and concentrated in vacuo. The crude material was purified on a silica gel cartridge (24 g) using an EtOAc/Hex gradient (0-100% EtOAc over 13CV). Isolated product fractions were concentrated and dried in vacuo to afford 180 mg of ethyl 3-azido-1-(4-octylbenzyl)-2-oxopyrrolidine-3-carboxylate.

Example 3

To a mixture of ethyl 3-azido-1-(4-octylbenzyl)-2-oxopyrrolidine-3-carboxylate (180 mg, 0.449 mmol) in EtOH (10 mL) was added sodium borohydride (68.0 mg, 1.798 mmol). The reaction mixture was stirred for 1 hour. The reaction was quenched with water. The reaction mixture was diluted with ethyl acetate and washed with saturated NaCl. The organic layer was dried with MgSO₄, filtered and concentrated. The solid material was dissolved in EtOH (10 mL) and Pearlman's Catalyst (63.1 mg, 0.449 mmol) was added. The reaction mixture was placed under a balloon of H₂ for 1 hour.

The mixture was filtered and purified. HPLC conditions: Phenomenex Luna 5 micron C18 column (30×100 mm); MeCN (0.1% TFA)/water (0.1% TFA); 20%-100% gradient over 15 minutes; 30 mL/min. Fractions with correct mass were isolated and freeze-dried overnight to afford 33 mg of 3-amino-3-(hydroxymethyl)-1-(4-octylbenzyl)pyrrolidin-2-one, TFA. $^1$H NMR (400 MHz, METHANOL-d4) δ 7.21 (d, J=2.6 Hz, 4H), 4.49 (s, 2H), 3.84-3.68 (m, 2H), 3.38 (dd, J=9.1, 4.5 Hz, 2H), 2.68-2.56 (m, 2H), 2.53 (dt, J=13.5, 4.6 Hz, 1H), 2.10 (dt, J=13.5, 9.2 Hz, 1H), 1.71-1.54 (m, 2H), 1.42-1.22 (m, 10H), 0.95-0.86 (m, 3H). HPLC Ret. Time=8.03/15.0 min (condition JG-H); LC/MS M$^{+1}$=333.

Examples 4 and 5

3-amino-3-(hydroxymethyl)-1-(4-octylbenzyl)pyrrolidin-2-one

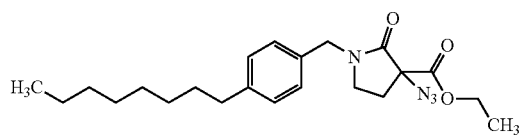

(4 and 5)

The racemic mixture of Example 3 (3-amino-3-(hydroxymethyl)-1-(4-octylbenzyl)pyrrolidin-2-one, TFA (18 mg)) was separated using chiral SFC conditions. Instrument: Berger SFC MGII (LVL-L4021 Lab); Column: Chiral OD-H 25×3 cm ID, 5 μm; Flow rate: 85.0 mL/min; Mobile Phase: 85/15 CO₂/MeOH w/0.1% DEA; Detector Wavelength: 220 nm (Lambda max); Sample Prep and Inj. Volume: 750 μL of 18 mg dissolved in 3.5 mL MeOH.

Example 4: PK-1 (6 mg): HPLC Ret. Time: 7.91 min (condition JG-I), LC/MS M$^{+1}$=333.

Example 5: PK-2 (5 mg): HPLC Ret. Time: 7.89 min (condition JG-I), LC/MS M$^{+1}$=333.

Example 6

3-amino-3-(hydroxymethyl)-1-(4-octylphenyl)pyrrolidin-2-one

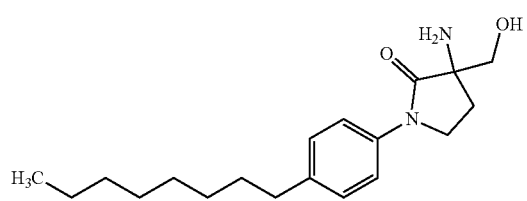

(6)

Preparation 6A: Methyl 1-(4-octylphenyl)-2-oxopyrrolidine-3-carboxylate

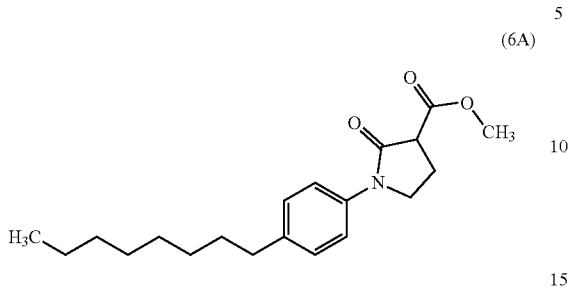

(6A)

To a mixture of 6,6-dimethyl-5,7-dioxaspiro(2.5)octane-4,8-dione (0.170 g, 1 mmol) in EtOH (1 mL) was added 4-octylbenzenamine (0.686 mL, 3 mmol). The reaction mixture was microwaved for 5 minutes at 100° C. LCMS showed a large peak with desired product mass. The reaction mixture was allowed to cool and a white solid formed. The solid was collected by filtration and washed with ether. LCMS showed a mixture of desired product and starting aniline. The filtrate was concentrated and all material was recombined.

To a mixture of 1-(4-octylphenyl)-2-oxopyrrolidine-3-carboxylic acid (317 mg, 1 mmol) in MeOH was bubbled HCl(g) for 5 minutes. Reaction mixture was stirred at room temperature for 1 hour. The solvents were removed in vacuo. The reaction mixture was diluted with ethyl acetate and washed with 1M HCl (2×). The organic layer was dried MgSO$_4$, filtered and concentrated to afford 320 mg of methyl 1-(4-octylphenyl)-2-oxopyrrolidine-3-carboxylate. LCMS shows desired product mass and adequate purity.

Preparation 6B: Methyl 3-bromo-1-(4-octylphenyl)-2-oxopyrrolidine-3-carboxylate

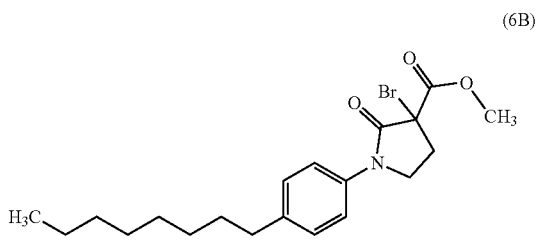 [SMILES: CCCCCCCCc1ccc(N2CCC(Br)(C(=O)OC)C2=O)cc1]

(6B)

To a mixture of methyl 1-(4-octylphenyl)-2-oxopyrrolidine-3-carboxylate (320 mg, 0.965 mmol) in THF (20 mL) was added sodium hydride (97 mg, 2.414 mmol). After bubbling ceased, NBS (258 mg, 1.448 mmol) was added. The reaction mixture was stirred for one hour. The reaction was quenched with water. The reaction mixture was diluted with ethyl acetate and washed with saturated NaCl. The organic layer was dried MgSO$_4$, filtered and concentrated. The crude material was purified on a silica gel cartridge (40 g) using an EtOAc/Hex gradient (0-100% EtOAc over 6CV then kept at 100%). Product fractions were isolated, concentrated and dried in vacuo to afford 160 mg of methyl 3-bromo-1-(4-octylphenyl)-2-oxopyrrolidine-3-carboxylate. NMR was consistent with desired product.

Preparation 6C: Methyl 3-azido-1-(4-octylphenyl)-2-oxopyrrolidine-3-carboxylate

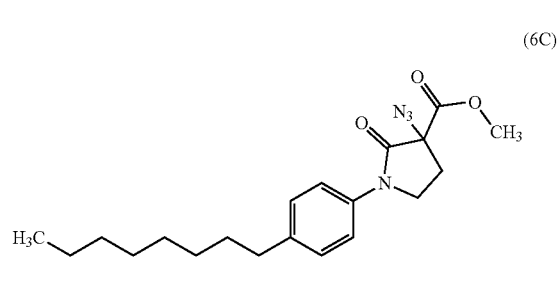 [SMILES: CCCCCCCCc1ccc(N2CCC(N=[N+]=[N-])(C(=O)OC)C2=O)cc1]

(6C)

To a mixture of methyl 3-bromo-1-(4-octylphenyl)-2-oxopyrrolidine-3-carboxylate (160 mg, 0.390 mmol) in DME was added sodium azide (50.7 mg, 0.780 mmol). The reaction mixture was heated to 90° C. for 2 hours. The reaction mixture was diluted with ethyl acetate and washed with saturated NaCl. The organic layer was dried with MgSO$_4$, filtered and concentrated to afford 140 mg of methyl 3-azido-1-(4-octylphenyl)-2-oxopyrrolidine-3-carboxylate.

Preparation 6D: 3-azido-3-(hydroxymethyl)-1-(4-octylphenyl)pyrrolidin-2-one

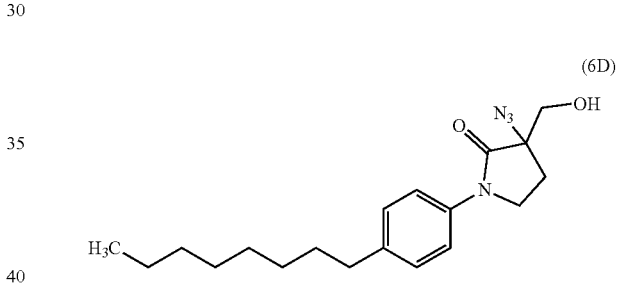

(6D)

To a mixture of methyl 3-azido-1-(4-octylphenyl)-2-oxopyrrolidine-3-carboxylate (145 mg, 0.39 mmol) in MeOH (10 mL) was added sodium borohydride (73.8 mg, 1.950 mmol). The reaction mixture was stirred at room temperature for 2 hours. The reaction was quenched with water. The reaction mixture was diluted with ethyl acetate and washed with saturated NaCl. The organic layer was dried with MgSO$_4$, filtered, and concentrated to afford 130 mg of 3-azido-3-(hydroxymethyl)-1-(4-octylphenyl) pyrrolidin-2-one.

Example 6

To a mixture of 3-azido-3-(hydroxymethyl)-1-(4-octylphenyl)pyrrolidin-2-one (130 mg, 0.377 mmol) in MeOH (20 mL) was added 10% Pd/C (40.2 mg, 0.377 mmol). The reaction mixture was placed under a balloon of H$_2$ for 1 hour. The H$_2$ was removed and the mixture was filtered to remove Pd and purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Fractions with correct mass were isolated and freeze-dried overnight to afford 66 mg of 3-amino-3-(hydroxymethyl)-1-(4-octylphenyl)pyrrolidin-2-one. HPLC Ret. Time: 8.95 min (condition JG-H), LC/MS M$^{+1}$=319.

Examples 7 and 8

3-amino-3-(hydroxymethyl)-1-(4-octylphenyl)pyrrolidin-2-one

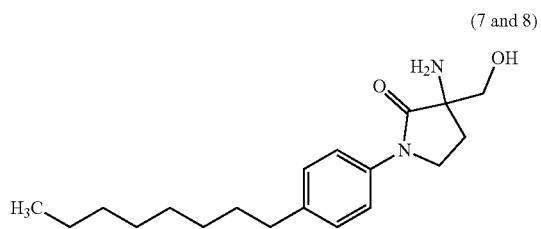 [SMILES: CCCCCCCCc1ccc(N2CCC(N)(CO)C2=O)cc1]

(7 and 8)

The racemic mixture of Example 6 (3-amino-3-(hydroxymethyl)-1-(4-octylphenyl)pyrrolidin-2-one (60 mg)) was separated using chiral SFC conditions. Preparative Chromatographic Conditions: Instrument: Berger SFC MGII (LVL-L4021 Lab). Column: Lux Cell 4, 25×3 cm ID, 5 mm; Flow rate: 85.0 mL/min; Mobile Phase: 78/22 $CO_2$/MeOH-0.1DEA; Detector Wavelength: 220 nm; Sample Prep and Inj. Volume: 10004 of 60 mg dissolved in 5 mL MeOH.

Example 7: PK-1 (16 mg): $^1$H NMR (400 MHz, METHANOL-d4) δ 7.54 (d, J=8.6 Hz, 2H), 7.22 (d, J=8.6 Hz, 2H), 3.93-3.79 (m, 2H), 3.71 (d, J=10.8 Hz, 1H), 3.55 (d, J=10.6 Hz, 1H), 2.69-2.55 (m, 2H), 2.53-2.38 (m, 1H), 2.08 (dt, J=13.3, 8.1 Hz, 1H), 1.63 (t, J=7.4 Hz, 2H), 1.42-1.23 (m, 10H), 1.02-0.82 (m, 3H). HPLC Ret. Time: 8.7/15 min (condition JG-H), LC/MS $M^{+1}$=319.

Example 8: PK-2 (14 mg): $^1$H NMR in $CD_3OD$ is consistent with desired product (400 MHz, METHANOL-d4) δ 7.54 (d, J=8.6 Hz, 2H), 7.22 (d, J=8.6 Hz, 2H), 3.91-3.80 (m, 2H), 3.71 (d, J=10.6 Hz, 1H), 3.56 (d, J=10.6 Hz, 1H), 2.62 (t, J=7.6 Hz, 2H), 2.47 (ddd, J=13.0, 6.5, 5.3 Hz, 1H), 2.08 (dt, J=13.3, 8.1 Hz, 1H), 1.63 (t, J=7.3 Hz, 2H), 1.42-1.24 (m, 10H), 0.95-0.84 (m, 3H). HPLC Ret. Time: 8.66/15 min (condition JG-H), LC/MS $M^{+1}$=319.

The Examples in Table 1 were prepared according to the general procedure for Examples 6-8.

TABLE 1

| Ex. No. | Structure | MW | HPLC ret. time (min.) | MS ($M^{+1}$) | Comment |
|---|---|---|---|---|---|
| 9 | 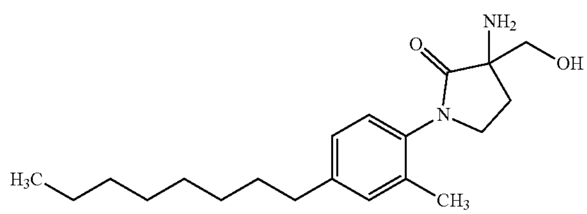 [SMILES: CCCCCCCCc1ccc(N2CCC(N)(CO)C2=O)c(C)c1] | 332.5 | 8.95 | 333.4 | racemic |
| 10 | 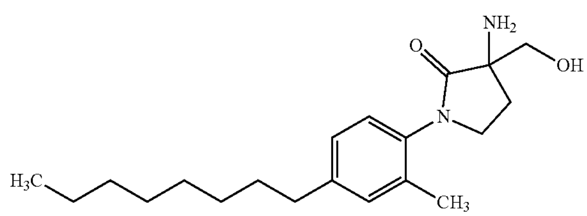 [SMILES: CCCCCCCCc1ccc(N2CCC(N)(CO)C2=O)c(C)c1] | 332.5 | 8.95 | 333.4 | PK-2 |
| 11 | 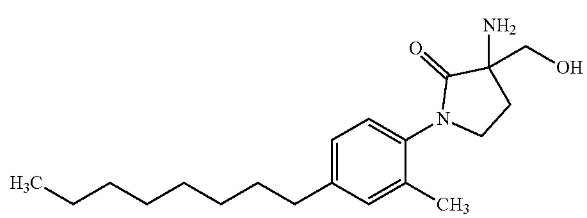 [SMILES: CCCCCCCCc1ccc(N2CCC(N)(CO)C2=O)c(C)c1] | 332.5 | 8.95 | 333.4 | PK-1 |
| 12 | 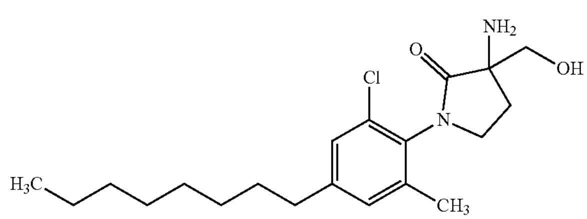 [SMILES: CCCCCCCCc1cc(C)c(N2CCC(N)(CO)C2=O)c(Cl)c1] | 387.3 | 10.3 | 388.2 | racemic |

TABLE 1-continued

| Ex. No. | Structure | MW | HPLC ret. time (min.) | MS (M+1) | Comment |
|---|---|---|---|---|---|
| 13 | 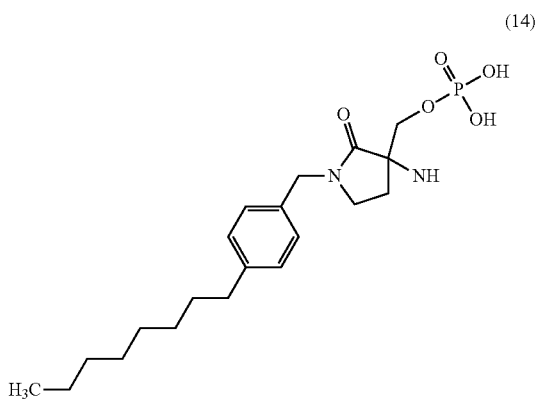 [SMILES: CCCCCCCCc1ccc(CN2CCC(N)(COP(=O)(O)O)C2=O)cc1] | 346.5 | 9.93 | 347.4 | racemic |

HPLC condition: JG-H

Example 14

(3-amino-1-(4-octylbenzyl)-2-oxopyrrolidin-3-yl)methyl dihydrogen phosphate (14)

To a mixture of 3-amino-3-(hydroxymethyl)-1-(4-octylbenzyl)pyrrolidin-2-one (10 mg, 0.030 mmol) in acetonitrile (1 mL) was added pyrophosphoryl chloride (0.042 mL, 0.301 mmol). The mixture was stirred overnight. LCMS showed that the reaction was incomplete. Additional pyrophosphoryl chloride (0.042 mL, 0.301 mmol) was added and the mixture was stirred for 1 hour. The reaction was quenched with water. The reaction mixture was purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Isolated fractions were obtained with correct mass and were freeze-dried overnight to afford 6 mg of Example 14. $^1$H NMR (400 MHz, METHANOL-d4) δ 7.21 (s, 4H), 4.62-4.35 (m, 2H), 4.15-3.91 (m, 2H), 3.54-3.36 (m, 3H), 2.79-2.53 (m, 3H), 1.63 (d, J=7.3 Hz, 2H), 1.43-1.19 (m, 10H), 1.00-0.83 (m, 3H). HPLC Ret. time=7.74 min (condition JG-H); LC/MS M$^{+1}$=413.3.

The Examples in Table 2 were prepared according to the general procedure for Example 14.

TABLE 2

| Ex. No. | Structure | MW | HPLC ret. time (min.) | HPLC condition | MS (M+1) |
|---|---|---|---|---|---|
| 15 | 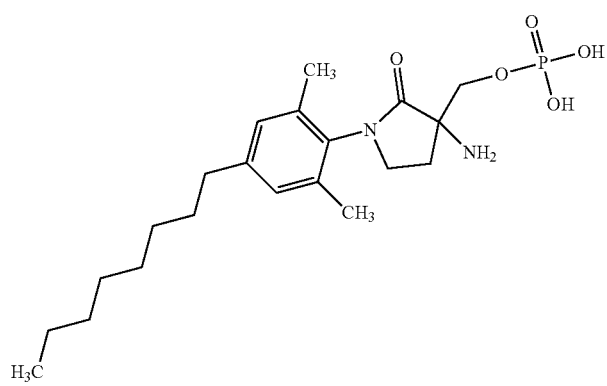 [SMILES: CCCCCCCCc1cc(C)c(N2CCC(N)(COP(=O)(O)O)C2=O)c(C)c1] | 426.5 | 1.4 | JG-G | 428.3 |

TABLE 2-continued

| Ex. No. | Structure | MW | HPLC ret. time (min.) | HPLC condition | MS (M$^{+1}$) |
|---|---|---|---|---|---|
| 16 | 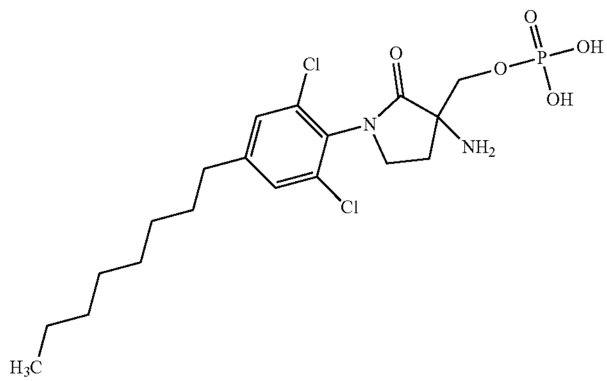 [SMILES: CCCCCCCCc1cc(Cl)c(N2CCC(N)(COP(=O)(O)O)C2=O)c(Cl)c1] | 467.3 | 8.9 | JG-H | 468.2 |
| 17 | 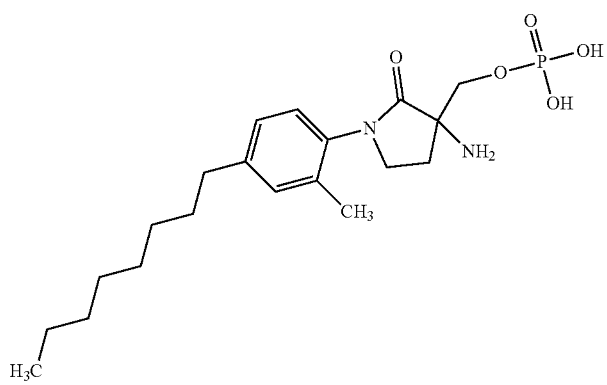 [SMILES: CCCCCCCCc1ccc(N2CCC(N)(COP(=O)(O)O)C2=O)c(C)c1] | 412.5 | 7.65 | JG-H | 413.4 |
| 18 | 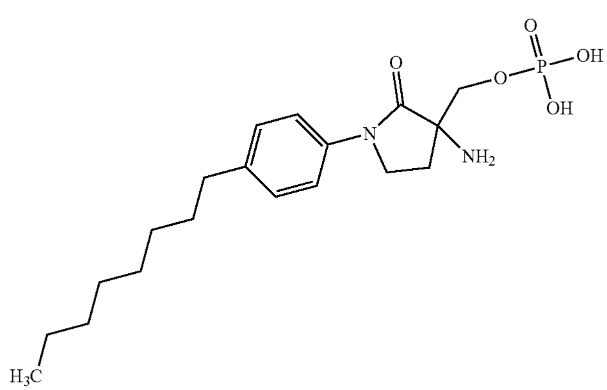 [SMILES: CCCCCCCCc1ccc(N2CCC(N)(COP(=O)(O)O)C2=O)cc1] | 398.4 | 7.67 | JG-H | 399.3 |

Comparative Example 19

(3-amino-1-(4-octylbenzyl)pyrrolidin-3-yl)methanol

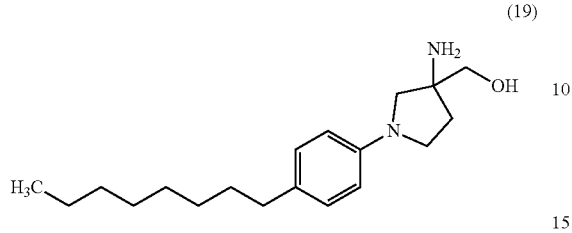
(19)

Preparation 19A: 1-(4-octylphenyl)pyrrolidin-3-ol

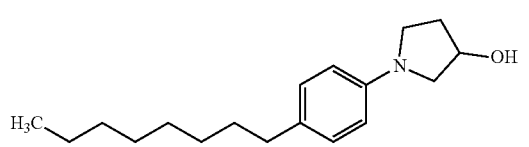
(19A)

To a mixture of 4-octylaniline (0.5 ml, 2.187 mmol) and potassium carbonate (363 mg, 2.62 mmol) in water was added 1,4-dibromobutan-2-ol (0.304 ml, 2.62 mmol). The reaction mixture was heated at 100° C. for 12 h. The reaction mixture was diluted with ethyl acetate and washed with saturated $KH_2PO_4$. The organic layer was dried $MgSO_4$, filtered and concentrated. The crude material was purified on a silica gel cartridge (40 g) using an EtOAc/Hex gradient (0-100% EtOAc over 12 CV). The isolated product fractions were concentrated and dried in vacuo to afford 310 mg of 1-(4-octylphenyl)pyrrolidin-3-ol.

Preparation 19B: 1-(4-octylphenyl)pyrrolidin-3-one

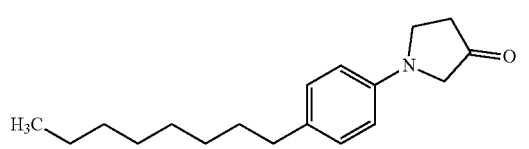
(19B)

Oxalyl chloride (0.306 mL, 3.50 mmol) was dissolved in DCM (20 mL) and the mixture was cooled to −78° C. DMSO (0.390 mL, 5.50 mmol) was added dropwise, and the reaction mixture was allowed to stir for 5 min. A solution of 1-(4-octylphenyl) pyrrolidin-3-ol (689 mg, 2.5 mmol) in DCM (3 mL) was added over 5 min and the reaction mixture was stirred for an additional 40 min. Next, TEA (41.2 ml, 295 mmol) was added. After 5 min, the reaction mixture was allowed to warm to room temperature. The reaction mixture was transferred to a separatory funnel and washed with 1N HCl. The phases were separated, and the aqueous phase was extracted with several portions of DCM. The combined organic extracts were washed with saturated $NaHCO_3$ and brine, dried over $MgSO_4$, and concentrated by rotary evaporation. The crude material was purified on a silica gel cartridge (40 g) using an EtOAc/Hexane gradient (0-100% EtOAc over 12 CV). Isolated product fractions, concentrated and dried in vacuo to afford 430 mg of 1-(4-octylphenyl) pyrrolidin-3-one.

Preparation 19C: 7-(4-octylphenyl)-1,3,7-triazaspiro [4.4]nonane-2,4-dione

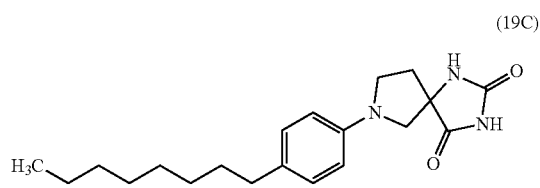 [SMILES: CCCCCCCCc1ccc(N2CCC3(C2)NC(=O)NC3=O)cc1]
(19C)

To a mixture of 1-(4-octylphenyl)pyrrolidin-3-one (430 mg, 1.573 mmol) and potassium cyanide (154 mg, 2.359 mmol) in EtOH (30 mL) and water (10 mL) in a stainless steel pressure bomb was added ammonium carbonate (378 mg, 3.93 mmol). The reaction vessel was sealed and heated at 90° C. overnight. The reaction vessel was cooled and the pressure was released. Water was added. Solid material precipitated and was collected and dried in vacuo to afford 260 mg of 7-(4-octylphenyl)-1,3,7-triazaspiro [4.4] nonane-2,4-dione.

Preparation 19D: 3-amino-1-(4-octylphenyl)pyrrolidine-3-carboxylic acid

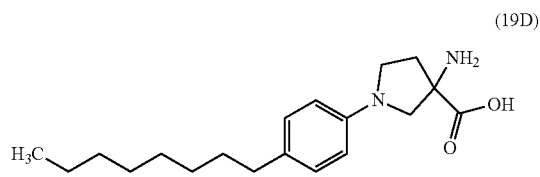 [SMILES: CCCCCCCCc1ccc(N2CCC(N)(C(=O)O)C2)cc1]
(19D)

To a mixture of 7-(4-octylphenyl)-1,3,7-triazaspiro[4.4] nonane-2,4-dione (260 mg, 0.757 mmol) in dioxane (10 mL) was added 2N NaOH (10 mL). The mixture was heated at reflux for 3 days. The mixture was cooled to room temperature. The pH was adjusted to ~6-7. The solid material was collected and dried in vacuo to afford 239 mg of 3-amino-1-(4-octylphenyl)pyrrolidine-3-carboxylic acid.

Preparation 19E: methyl 3-amino-1-(4-octylphenyl)pyrrolidine-3-carboxylate

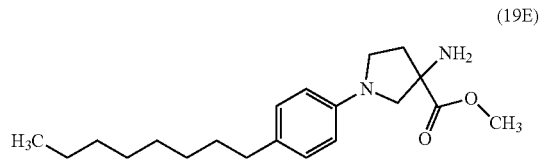 [SMILES: CCCCCCCCc1ccc(N2CCC(N)(C(=O)OC)C2)cc1]
(19E)

To a mixture of 3-amino-1-(4-octylphenyl)pyrrolidine-3-carboxylic acid (239 mg, 0.75 mmol) in MeOH (10 mL) was bubbled HCl (g) for 10 minutes. The reaction mixture was heated at 80° C. overnight. The mixture was cooled and about half of solvent was removed. The pH was adjusted to −7. The mixture was extracted with EtOAc (2×). The organic layer was dried MgSO$_4$, filtered and concentrated to afford 168 mg of methyl 3-amino-1-(4-octylphenyl) pyrrolidine-3-carboxylate.

Comparative Example 19

To a mixture of methyl 3-amino-1-(4-octylphenyl)pyrrolidine-3-carboxylate (168 mg, 0.505 mmol) in MeOH (5 mL) was added sodium borohydride (96 mg, 2.53 mmol). The reaction mixture was stirred at room temperature overnight. The reaction was quenched with water. The reaction mixture was diluted with MeCN, filtered, and purified by HPLC. HPLC conditions: Phenomenex Luna C18 5 micron column (250×30 mm); 25-100% CH$_3$CN/water (0.1% TFA); 25 minute gradient; 30 mL/min. Isolated fractions with correct mass were collected and freeze-dried overnight to afford 80 mg of (3-amino-1-(4-octylphenyl)pyrrolidin-3-yl) methanol, TFA.

The material (3-amino-1-(4-octylphenyl)pyrrolidin-3-yl) methanol, TFA (32 mg, 0.076 mmol) was re-purified by HPLC. HPLC conditions: Phenomenex Luna 5 micron C18 column (30×100 mm); MeCN (0.1% TFA)/water (0.1% TFA); 20%-100% gradient over 15 minutes; 30 mL/min. Isolated fractions with correct mass were collected and freeze-dried overnight to afford 22 mg of (3-amino-1-(4-octylphenyl)pyrrolidin-3-yl) methanol, TFA. $^1$H NMR (400 MHz, METHANOL-d4) δ 7.05 (d, J=8.6 Hz, 2H), 6.61 (d, J=8.6 Hz, 2H), 3.76 (d, J=2.0 Hz, 2H), 3.60 (ddd, J=9.4, 8.4, 6.5 Hz, 1H), 3.51-3.35 (m, 3H), 2.52 (t, J=7.5 Hz, 2H), 2.35-2.13 (m, 2H), 1.57 (t, J=7.2 Hz, 2H), 1.39-1.24 (m, 10H), 0.99-0.85 (m, 3H). HPLC Ret. Time=0.96/2.0 min (condition JG-G); LC/MS M$^{+1}$=305.

S1P$_1$ Binding Assay:

Membranes were prepared from CHO cells expressing human S1P$_1$. Cells pellets (1×10$^9$ cells/pellet) were suspended in buffer containing 20 mM HEPES (4-(2-hydroxyethyl)-1-piperazineethanesulfonic acid), pH 7.5, 50 mM NaCl, 2 mM EDTA (Ethylenediamine tetraacetic acid) and Protease Inhibitor cocktail (Roche), and disrupted on ice using the Polytron homogenizer. The homogenate was centrifuged at 20,000 rpm (48,000 g) and the supernatant was discarded. The membrane pellets were resuspended in buffer containing 50 mM HEPES, pH 7.5, 100 mM NaCl, 1 mM MgCl$_2$, 2 mM EDTA and stored in aliquots at −80° C. after protein concentration determination.

Membranes (2 μg/well) and 0.03 nM final concentration of $^{33}$P-S1P ligand (1 mCi/ml, Perkin Elmer or American Radiolabeled Chemicals) diluted in assay buffer (50 mM HEPES, pH7.4, 5 mM MgCl$_2$, 1 mM CaCl$_2$, 0.5% fatty acid free BSA(bovine serum albumin), 1 mM NaF) were added to the compound plates (384 Falcon v-bottom plate (0.5 μl/well in a 11 point, 3-fold dilution). Binding was performed for 45 minutes at room temperature, terminated by collecting the membranes onto 384-well Millipore FB filter plates, and radioactivity was measured by TOPCOUNT®. The competition data of the test compounds over a range of concentrations was plotted as percentage inhibition of radioligand specific binding. The IC$_{50}$ is defined as the concentration of competing ligand needed to reduce specific binding by 50%.

Receptor [$^{35}$S] GTPγS Binding Assays:

Compounds were loaded in a 384 Falcon v-bottom plate (0.5 μL/well in a 11 point, 3-fold dilution). Membranes prepared from S1P$_1$/CHO cells or EDG3-Gal5-bla HEK293T cells (EDG3 equivalent S1P$_3$) were added to the compound plate (40 μL/well, final protein 3 μg/well) with MULTIDROP®. [$^{35}$S]GTP (1250 Ci/mmol, Perkin Elmer)

| Comparative Ex. No. | Structure | MW | HPLC ret. time (min.) | HPLC condition | MS (M$^{+1}$) |
|---|---|---|---|---|---|
| 20 | 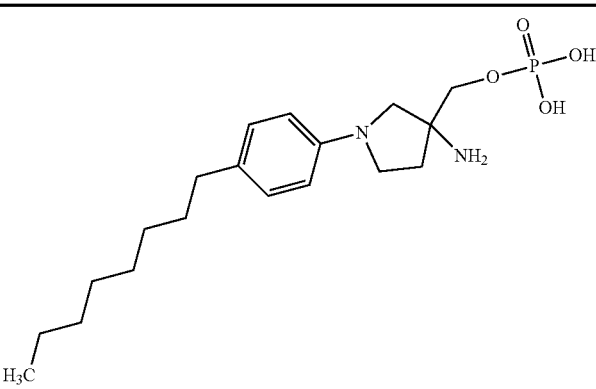 | 384.5 | 3.66 | JG-CC | 385.0 |

BIOLOGICAL ASSAYS

The compounds of Formula (I) or salts thereof engage their biological targets (e.g. S1P1) after bioactivation through phosphorylation of the alcohol to provide active phosphate ester compounds of Formula (I) or salts thereof. In vitro characterization of biological activity of the examples was conducted on synthetically prepared samples of the phosphorylated compounds.

was diluted in assay buffer: 20 mM HEPES, pH7.5, 10 mM MgCl$_2$, 150 mM NaCl, 1 mM EGTA(ethylene glycol tetraacetic acid), 1 mM DTT (dithiothreitol), 10 μM GDP, 0.1% fatty acid free BSA, and 10 μg/ml Saponin to 0.4 nM. 40 μL of the [$^{35}$S] GTP solution was added to the compound plate with a final concentration of 0.2 nM. The reaction was kept at room temperature for 45 min. At the end of incubation, all the mixtures in the compound plate were transferred to Millipore 384-well FB filter plates via the VELOCITY11®

Vprep liquid handler. The filter plate was washed with water 4 times by using the manifold Embla plate washer and dried at 60° C. for 45 min. MicroScint 20 scintillation fluid (30 µL) was added to each well for counting on the Packard TOPCOUNT®. $EC_{50}$ is defined as the agonist concentration that corresponds to 50% of the Ymax (maximal response) obtained for each individual compound tested.

A smaller value for GTPγS $S1P_1$ $EC_{50}$ value indicated greater activity for the compound in the GTPγS $S1P_1$ binding assay. Thus the compounds of the present invention may be used in treating, preventing, or curing various $S1P_1$ receptor-related conditions. The compounds have potential use in treating, preventing, or curing autoimmune and inflammatory diseases such as multiple sclerosis, rheumatoid arthritis, inflammatory bowel disease, lupus, psoriasis, or minimizing or reducing rejection of transplanted organs.

As shown in Table A, Examples 14 and 17 offered a significant improvement in GTPγS $S1P_1$ $EC_{50}$ value as compared to Comparative Compound 20, (3-amino-1-(4-octylphenyl)pyrrolidin-3-yl)methyl dihydrogen phosphate; US 2009/0029947).

TABLE A

| Ex. | GTPγS $S1P_1$ $EC_{50}$ (nM) | GTPγS $S1P_3$ $EC_{50}$ (nM) |
|---|---|---|
| 14 | 41 | >30,000 |
| 15 | 14393 | >60,000 |
| 17 | 161 | >60,000 |
| 18 | 454 | >60,000 |
| 20 | 384 | >30,000 |

What is claimed is:

1. A compound of Formula (I):

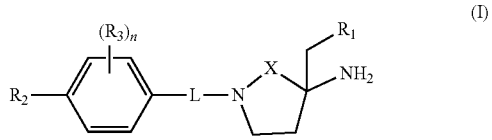

(I)

or a salt thereof, wherein:
X is —$CH_2$— or —C(O)—;
$R_1$ is —OH or —OP(O)(OH)$_2$;
L is a bond, —$CH_2$—, or —C(O)—;
$R_2$ is n-$C_{6-8}$ alkyl;
each $R_3$ is independently selected from Cl and —$CH_3$; and
n is zero, 1, or 2;
provided that if X is —$CH_2$—, then L is —$CH_2$— or —C(O)—.

2. The compound according to claim 1 or a salt thereof, wherein X is —C(O)—.

3. The compound according to claim 1 or a salt thereof, wherein:
L is —$CH_2$— or —C(O)—.

4. The compound according to claim 1 or a salt thereof, wherein:
X is —$CH_2$—;
L is —$CH_2$— or —C(O)—; and
$R_2$ is n-$C_8$ alkyl.

5. The compound according to claim 1 or a salt thereof, wherein:
X is —C(O)—;
L is a bond, —$CH_2$—, or —C(O)—; and
$R_2$ is n-$C_8$ alkyl.

6. The compound according to claim 1 or a salt thereof, wherein:
X is —C(O)—;
L is a bond; and
$R_2$ is n-$C_8$ alkyl.

7. The compound according to claim 1 or a salt thereof, wherein said compound is: (3-amino-3-(hydroxymethyl)pyrrolidin-1-yl)(4-octylphenyl)methanone (1); (3-amino-1-(4-octylbenzyl)pyrrolidin-3-yl)methanol (2); 3-amino-3-(hydroxymethyl)-1-(4-octylbenzyl) pyrrolidin-2-one, TFA (3-5); 3-amino-3-(hydroxymethyl)-1-(4-octylphenyl)pyrrolidin-2-one (6-8); 3-amino-3-(hydroxymethyl)-1-(2-methyl-4-octylphenyl)pyrrolidin-2-one (9); 3-amino-3-(hydroxymethyl)-1-(2-methyl-4-octylphenyl)pyrrolidin-2-one (10); 3-amino-3-(hydroxymethyl)-1-(2-methyl-4-octylphenyl)pyrrolidin-2-one (11); 3-amino-1-(2,6-dichloro-4-octylphenyl)-3-(hydroxymethyl)pyrrolidin-2-one (12); or 3-amino-1-(2,6-dimethyl-4-octylphenyl)-3-(hydroxymethyl)pyrrolidin-2-one (13).

8. The compound according to claim 1 or a salt thereof, wherein said compound is: (3-amino-1-(4-octylbenzyl)-2-oxopyrrolidin-3-yl)methyl dihydrogen phosphate (14); (3-amino-1-(2,6-dimethyl-4-octylphenyl)-2-oxopyrrolidin-3-yl)methyl dihydrogen phosphate (15); (3-amino-1-(2,6-dichloro-4-octylphenyl)-2-oxopyrrolidin-3-yl)methyl dihydrogen phosphate (16); (3-amino-1-(2-methyl-4-octylphenyl)-2-oxopyrrolidin-3-yl) methyl dihydrogen phosphate (17); or (3-amino-1-(4-octylphenyl)-2-oxopyrrolidin-3-yl) methyl dihydrogen phosphate (18).

9. A pharmaceutical composition comprising a compound according to claim 1 or a pharmaceutically-acceptable salt thereof and a pharmaceutically acceptable carrier.

10. A method of treating an autoimmune disease or a chronic inflammatory disease, comprising administering to a mammalian patient a compound according to claim 1 or a pharmaceutically acceptable salt thereof.

11. The method according to claim 10 wherein said autoimmune disease or a chronic inflammatory disease is selected from lupus, multiple sclerosis, inflammatory bowel disease, Sjögren's syndrome, and rheumatoid arthritis.

12. The compound according to claim 1 or a salt thereof, wherein:
X is —$CH_2$—; and
L is —$CH_2$— or —C(O)—.

13. The compound according to claim 1 or a salt thereof, wherein:
X is —C(O)—; and
L is a bond, —$CH_2$—, or —C(O)—.

14. The compound according to claim 1 or a salt thereof, wherein:
X is —C(O)—; and
L is a bond.

* * * * *